United States Patent
Xiao et al.

(10) Patent No.: US 6,706,937 B2
(45) Date of Patent: Mar. 16, 2004

(54) CONVERSION OF AROMATIC HYDROCARBONS

(75) Inventors: Xin Xiao, Houston, TX (US); James R. Butler, Friendwood, TX (US)

(73) Assignee: Fina Technology, Inc., Houston, TX (US)

( * ) Notice: Subject to any disclaimer, the term of this patent is extended or adjusted under 35 U.S.C. 154(b) by 51 days.

(21) Appl. No.: 10/167,096

(22) Filed: Jun. 11, 2002

(65) Prior Publication Data

US 2003/0229258 A1 Dec. 11, 2003

(51) Int. Cl.[7] .................................................. C07C 5/22
(52) U.S. Cl. ....................................... 585/475; 585/470
(58) Field of Search ................................. 585/475, 470

(56) References Cited

U.S. PATENT DOCUMENTS

| | | | |
|---|---|---|---|
| 4,956,511 A | 9/1990 | Butler et al. ................. | 585/475 |
| 5,457,180 A | 10/1995 | Zacharie ..................... | 530/333 |
| 5,475,180 A | * 12/1995 | Shamshoum et al. ....... | 585/475 |

* cited by examiner

Primary Examiner—Thuan D. Dang
(74) Attorney, Agent, or Firm—William D. Jackson; Bradley A. Misley

(57) ABSTRACT

A process for the transalkylation of an aromatic feedstock containing a benzene component and a polyalkylated aromatic component comprising at least one polyalkyl aromatic compound of at least nine carbon atoms. The feedstock is supplied to a reaction zone containing a metal modified zeolite transalkylation catalyst. The reaction zone is operated under conditions providing an equivalent conversion of pure toluene in the presence of the catalyst within the range of 40–55%, resulting in a transalkylated product with a reduced polyalkyl benzene content and an enhance monoalkyl benzene content relative to the transalkylation feedstock. In continued operation of the transalkylation reaction zone, at least one of the reaction conditions of temperature, pressure, and space velocity is adjusted in order to maintain a constant reaction severity to provide a desired equivalent conversion of toluene within a tolerance range of ±2%. Specifically, the temperature is progressively increased while continuing the operation of the transalkylation zone to maintain a condition of constant reaction severity.

23 Claims, 2 Drawing Sheets

US 6,706,937 B2

CONVERSION OF AROMATIC HYDROCARBONS

FIELD OF THE INVENTION

The present invention involves the operation of an aromatic conversion unit in a manner to provide for the transalkylation of aromatic hydrocarbons in conjunction with or in reference to a toluene disproportionation reaction.

BACKGROUND OF THE INVENTION

Various processes involving the disproportionation of aromatic hydrocarbons are utilized in petroleum refining operations. One commonly utilized refining process involves the disproportionation of toluene in a transalkylation reaction in which toluene is converted to benzene and xylene. The disproportionation reaction which typically takes place in the presence of molecular hydrogen supplied in addition to the toluene provides for a stoichiometric relationship in which two moles of toluene are converted to one mole of benzene and one mole of xylene. The disproportionation reaction may be carried out over a metal modified zeolite disproportionation catalyst, such as mordenite modified by the inclusion of a metal such as nickel or palladium.

Another conversion reaction employed in petroleum refining operations involves the transalkylation of polyalkyl aromatic compounds with benzene to produce a transalkylation product having a diminished content of polyalkylated aromatics with an enhanced content of monoalkylated aromatic compounds. The resulting transalkylation product exhibits correspondingly reduced benzene content. Oftentimes, transalkylation reactions are carried out in an integrated process in which an aromatic substrate, such as benzene, is alkylated with an alkylating agent, such as ethylene or propylene, to produce ethylbenzene or propylbenzene together with polyalkylated aromatics, such as dialkyl and trialkyl benzenes. The polyalkyl aromatics are separated from the monoalkyl benzene recovered from the alkylation reactor and recycled to a downstream transalkylation reactor. Benzene is also supplied to the transalkylation reactor in order to produce a monoalkylated disproportionation product, along with other alkylated aromatic compounds.

SUMMARY OF THE INVENTION

In accordance with the present invention, there is provided a disproportionation transalkylation process utilizing a metal modified zeolite disproportionation catalyst. In carrying out the invention, there is provided a catalytic reaction zone containing a metal modified disproportionation catalyst. A toluene-containing feedstock is supplied to the reaction zone which is operated under temperature and pressure conditions effective for the disproportionation of toluene. A disproportionation product containing benzene and xylene is recovered from the reaction zone. At a suitable point in the process, the supply of toluene-containing feedstock to the reaction zone is terminated and the disproportionation procedure is shut down. Thereafter, a transalkylation feedstock is supplied to the reaction zone. The transalkylation feedstock contains a benzene component and a polyalkylated aromatic component comprising at least one polyalkylated aromatic compound having at least nine carbon atoms. The reaction zone is operated under conditions effective for the transalkylation of the feedstock to produce a transalkylated product having reduced polyalkylated benzene content and an enhanced monoalkyl benzene content.

In a preferred embodiment of the invention, the disproportionation catalyst comprises mordenite. Preferably the metal modified disproportionation catalyst comprises nickel-modified mordenite having a nickel content within the range of 0.1–2.0 wt. % of the mordenite. In a further aspect of the invention, the transalkylation feedstock has a weight ratio of the benzene component to the polyalkylated benzene component within the range of 1:9–2:1. In yet a further aspect of the invention, the transalkylation product recovered from the reaction zone comprises toluene, ethylbenzene, and xylene with a content of $C_7$ and $C_8$ alkyl aromatic compounds within the range of 35–45 wt. %. Preferably, the ethylbenzene content of the transalkylation product is less than one-half of the toluene content, and preferably and more specifically, also less than one-half of the xylene content.

In yet a further aspect of the invention, there is provided a process for the transalkylation of an aromatic feedstock containing a benzene component and a polyalkylated aromatic component comprising at least one polyalkyl aromatic compound of at least nine carbon atoms. The reaction zone is operated under temperature and pressure conditions providing an equivalent conversion of pure toluene in the presence of the catalyst within the range of 40–55%, resulting in a transalkylated product with a reduced polyalkyl benzene content and an enhance monoalkyl benzene content relative to the transalkylation feedstock. Preferably, the reaction zone is operated under pressure and temperature conditions providing for an equivalent conversion of pure toluene in the presence of the catalyst within the range of 42–48% and, more specifically, within the range of 45–47%. In continued operation of the transalkylation reaction zone, at least one of the reaction conditions of temperature, pressure, and space velocity is adjusted in order to maintain a constant reaction severity to provide a desired equivalent conversion of toluene within a tolerance range of ±2%. Preferably, the temperature is progressively increased while continuing the operation of the transalkylation zone to maintain a condition of constant reaction severity.

DETAILED DESCRIPTION OF THE INVENTION

Figure 1:
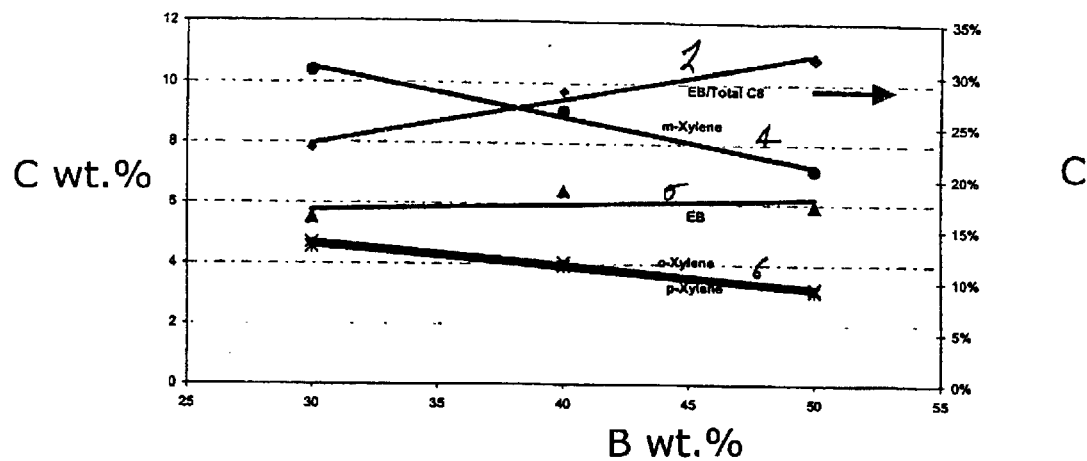
FIG. 1 is a graphical presentation showing $C_8$ yields of the transalkylation process as a function of the benzene content of the transalkylation feedstock.

The present invention provides processes which can be employed to effectively convert $C_9$+ aromatics into $C_7$–$C_8$ aromatics via transalkylation with benzene over a toluene disproportionation catalyst. The present invention can be carried out in conjunction with a toluene disproportionation procedure operated sequentially with the transalkylation procedure employing a common reaction zone, or it can be carried out as an independent stand-alone procedure. In either case, the invention can be carried out over metal modified zeolite catalyst which can be characterized in terms of conversion of pure toluene to benzene and xylene in accordance with the toluene disproportionation reaction.

Suitable toluene disproportionation procedures and the catalyst used there, which can be employed in the present invention, are disclosed in commonly assigned U.S. Pat. Nos. 4,956,511, 5,387,732, and 5,475,180. As disclosed in these patents, the toluene disproportionation catalysts take the form of metal modified zeolite transalkylation catalysts, specifically such molecular sieves as are promoted by the inclusion of a Group VIII metal, i.e. a metal found in Group VIII (CAS notation) of the Periodic Table of Elements. Particularly, metal modifiers incorporating nickel, palladium, and platinum are effective modifiers for use in toluene disproportionation. Molecular sieves (zeolites) useful in the disproportionation of toluene include mordenite catalysts modified by the inclusion of nickel, palladium, platinum, or other Group VIII metals, such as cobalt.

Suitable mordenite catalysts employed in the present invention may be natural mordenites of relatively low silica/alumina mole ratios of about 10 or less. Mordenite catalysts are described in *Kirk-Othmer Encyclopedia of Chemical Technology*, Third Edition, 1991, Vol. 15, pp. 638–643, under the heading "Molecular Sieves," the entire disclosure of which is incorporated herein by reference. Preferably, however, mordenite catalysts, which are somewhat aluminum-deficient to provide a silica/alumina mole ratio within the range of about ____–____, will be used in carrying out the invention. For a further description of toluene disproportionation processes involving metal modified mordenite catalysts, reference is made to the aforementioned U.S. Pat. Nos. 4,956,511, 5,387,723, and 5,475,180, the entire disclosures of which are incorporated herein by reference.

A suitable nickel modified mordenite catalyst, which can be employed in the present invention, is described in the aforementioned U.S. Pat. No. 4,956,511 and has a nickel content within the range of about 0.1–2.0 wt. % and preferably within the range of 0.5–1.5 wt. %. The nickel content of the mordenite catalyst is expressed in terms of the amount of nickel based upon the amount of zeolite present without reference to a binder, which will normally be employed to form the particulate catalyst prills actually incorporated into the reaction zone.

In the present invention the temperature and pressure conditions of the transalkylation reaction are controlled to provide a desired equivalent toluene conversion factor (ETCF) within the range of 40–55%. By the term "equivalent toluene conversion factor" is meant the amount in weight percent of toluene converted for a pure toluene feed at the reaction conditions (temperature, pressure, and space velocity) involved. Thus, by way of example, assume that the operation of the reaction zone at a temperature of 400° C. and a pressure of 40 atmospheres at a designated space velocity of 3 hrs.$^{-1}$ results in 45 wt. % toluene conversion in the disproportionation of a pure toluene feedstock. Then, using this same catalyst in the transalkylation of a feedstock of benzene and polyalkylated aromatics, the reaction conditions to achieve an equivalent toluene conversion factor of 45% would be a temperature of 400° C., a pressure of 40 atmospheres, and a space velocity of 3 hrs.$^{-1}$. Preferably, the transalkylation zone will be operated to provide a constant reaction severity at the desired ETCF value. Thus, if it is desired to maintain an ETCF of 45% over the course of the transalkylation reaction, at least one of the reaction conditions, normally temperature, will be adjusted to maintain the ETCF at 45%. As described below, typically the transalkylation reaction with fresh catalysts may start out at a relatively low temperature within an operating temperature range of about 370–460° C. and a desired pressure of 40 atmospheres. As the reaction proceeds with time, deactivation of the catalyst will occur, resulting in a reduced activity of the catalyst. Thus, in order to maintain the ETCF at the desired value of 45% and maintain a constant reaction severity, the reaction conditions may gradually be made more severe. Normally it will be desirable to maintain the pressure and space velocity constant and progressively increase the temperature. Hydrogen co-feed will normally be supplied during both of the toluene phases and the transalkylation phases involved in carrying out the present invention. Normally, the mole ratio of hydrogen co-feed to hydrocarbon feed will be within the range of 0.5–8.0 during toluene disproportionation and during transalkylation of the benzene heavy alkyl aromatic feedstock. As indicated by the experimental work described below, assuming the pressure and space velocity remain the same, the increase in temperature needed to maintain a constant reaction severity, i.e. a constant ETCF, will increase somewhat sharply early in the process until a midpoint is reached at which time the rate of increase in temperature necessary to maintain a constant reaction severity will level off. For example, the transalkylation process may be operated at a pressure of 40 atmospheres and an LHSV of 3 hrs.$^{-1}$ with an initial reaction temperature of 370° C. Assuming a ETCF value of 45%, in order to maintain constant reaction severity at this value, the temperature will be increased to an midpoint value of perhaps 405° C., after which it will begin to level off and increase at a more moderate rate until it reaches a value where the catalyst activity has degenerated to the point where the process is no longer deemed economically feasible. Typically, this value will be at a temperature of about 440° C.

In experimental work respecting the present invention, a protocol involving an initial toluene disproportionation procedure followed by three-sequential transalkylation procedures with intervening toluene disproportionation procedures was carried out employing a nickel mordenite catalyst having a nickel content, based upon the mordenite, of 1.0 wt. %. The mordenite catalyst had a silica/alumina ratio of about 18. The polyalkyl aromatic component employed in the transalkylation procedures contained about 76 wt. % $C_9$ aromatics, about 12 wt. % $C_8$ alkyl aromatics, and about 7 wt. % $C_{10}$ alkyl benzenes, with an average of 2.99 alkyl carbons per benzene ring. This feed stream, designated "$C_9$+Ar," had a composition as set forth in Table I.

TABLE I

| COMPONENT | WT. % |
| --- | --- |
| NONAROM | 0.0246 |
| BENZENE | 0.0056 |
| TOLUENE | 1.0086 |
| ETBENZENE | 0.0986 |
| p-XYLENE | 0.5243 |
| m-XYLENE | 1.4795 |
| o-XYLENE | 9.0606 |
| CUMENE | 0.5616 |
| n-PR-BZ | 5.9406 |
| Ets | 31.7556 |
| 1,3,5-TMB | 9.4735 |
| 1,2,4-TMB | 27.4495 |
| 1,2,3-TMB | 0.9528 |
| DEBs | 1.1045 |
| Bu-BZs | 0.0000 |
| UNKNOWN $C_{10}$ | 5.5721 |
| HEAVIES | 4.9879 |

In this experimental work a down flow reactor was loaded with fresh nickel mordenite catalysts as described above. The catalyst volume was 30 millimeters. The reactor was operated at a constant space velocity (LHSV) of 3 hrs.$^{-1}$ and a pressure of about 42 atmospheres absolute. The ratio of H₂ to the mole ratio of H₂ to hydrocarbon was 3:1 for the toluene disproportionation and also for the transalkylation runs. The toluene conversion factor and the equivalent toluene conversion factor were maintained over the life of the test at about 47% by adjusting the temperature as necessary. In carrying out this experimental work, a feedstock of 100% toluene was initially injected for 21 days. The feed was then switched to a mixture of 40 wt. % benzene and 60 wt. % C₉+Ar. In the third phase, the feed was switched back to toluene, and the temperature was increased to maintain 47% toluene conversion. In the next phase 30 wt. % benzene and 70 wt. % ArC₁₀ were introduced. This was followed by another toluene run before the mixture was switched to 50 wt. % benzene and 50 wt. % C₉+Ar. The overall test procedures, including the relative amounts of benzene, C₉+Ar, and toluene and the time on stream, are set forth in Table II.

TABLE II

Different Ratios of Benzene/C₉ + Ar Feed over UCI TDP Catalyst

| Test plan | Feed Composition, wt % | | | Testing Period |
|---|---|---|---|---|
| | Benzene | C₉ + Ar | Toluene | TOS, days |
| Step 1 | 0 | 0 | 100 | 0–21 |
| Step 2 | 40 | 60 | 0 | 21–34 |
| Step 3 | 0 | 0 | 100 | 34–43 |
| Step 4 | 30 | 70 | 0 | 43–58 |
| Step 5 | 0 | 0 | 100 | 58–63 |
| Step 6 | 50 | 50 | 0 | 63–76 |
| Step 7 | 0 | 0 | 100 | 76–79 |

As indicated above, constant reaction severity at an ETCF of 47% was maintained by adjusting the temperature at the conclusion of each step of the experimental protocol.

The results of the transalkylation of benzene with the C₉+Ar aromatic component under toluene disproportionation conditions are shown in Table III.

The data presented in Table III represents an average of about 10 data points for each feedstock comprising 30 wt. %, 40 wt. %, and 50 wt. % benzene with C₉+Ar forming the balance of the feedstock. The 40-wt % BZ feed is approximately equal molar of C₆:C₉ if the C₉+Ar is assumed as C₉. As can be seen, benzene and C₉+Ar were converted into toluene, xylenes, and ethylbenzene (EB), with a total $C_{7-8}$ product of 37–44 wt %. A typical product at 40 wt %-BZ/60 wt % C₉+Ar feed was: toluene, 19.4; EB, 6.4 and xylenes, 17.1 wt %. When benzene increased to 50 wt % in the feed, $C_{7-8}$ products decreased to 36.99 wt %. While maintaining 50% benzene in the feed, the reactor temperature was increased. The $C_{7-8}$ products increased to 43.75 wt % at this higher temperature, which was verified to be a condition equivalent to 53% toluene conversion.

From an examination of the feed and effluent composition for the 30% benzene and 70% C₉+Ar, it can be seen that benzene, ethyltoluene, trimethylbenzene, diethylbenzene, and other C₁₀ and heavies were converted into toluene, ethylbenzene, and xylenes. Toluene as a single component increased by 19%. Total xylenes increased from 12% to 20%, mostly in m-and p-xylenes. The o-xylene isomer, which is normally undesirable, was converted into equilibrium xylene isomers. Ethylbenzene increased from 0.5 to 5.5%, indicating transalkylation of benzene and ethyltoluene. Cumene and n-propylbenzene were converted over 90% via dealkylation, resulting in propane and benzene products. As the total of the TMB, ET, and DEB decreased, the respective isomers were redistributed into equilibrium. Unidentified C₁₀ aromatics decreased from 5.2 to 1.9% (other C₁₀). $C_{11+}$ heavies decreased about 1% (from 8.6 to 7.6%).

In an analysis of the experimental work reported herein, the conversion and yield of a Component A can be determined by Equations 1 and 2.

$$C_a = \frac{A_f - A_p}{A_f} \quad (1)$$

TABLE III

Feed and Effluent Composition of C6/C9 Transalkylation

| Condition | 47% Toluene Conversion Equivalent | | | | | | 53% Tol conv. Equivalent | |
|---|---|---|---|---|---|---|---|---|
| %-BZ in feed | 30 | | 40 | | 50 | | 50 | |
| Composition | Feed | Effluent | Feed | Effluent | Feed | Effluent | Feed | Effluent |
| Nonaromatics | 0.34 | 1.40 | 0.07 | 1.17 | 0.25 | 0.99 | 0.25 | 1.19 |
| Benzene | 28.41 | 22.06 | 39.38 | 30.19 | 49.71 | 40.96 | 48.48 | 38.47 |
| Toluene | 0.03 | 19.16 | 0.09 | 19.37 | 0.12 | 17.54 | 0.03 | 22.67 |
| Ethylbenzene | 0.53 | 5.52 | 0.50 | 6.42 | 0.46 | 5.93 | 0.46 | 5.91 |
| p-Xylene | 1.48 | 4.55 | 1.26 | 3.94 | 1.04 | 3.12 | 1.04 | 3.53 |
| m-Xylene | 3.86 | 10.36 | 3.30 | 9.07 | 2.73 | 7.16 | 2.72 | 8.03 |
| o-Xylene | 6.54 | 4.70 | 5.60 | 4.06 | 4.61 | 3.23 | 4.60 | 3.61 |
| Cumene | 0.31 | 0.02 | 0.27 | 0.05 | 0.22 | 0.03 | 0.22 | 0.02 |
| n-Propylbenzene | 2.83 | 0.13 | 2.41 | 0.40 | 1.98 | 0.19 | 1.98 | 0.10 |
| Ethyltoluene | 13.59 | 5.85 | 11.44 | 5.23 | 9.39 | 3.84 | 10.64 | 3.10 |
| Trimethylbenzene | 23.71 | 16.24 | 19.87 | 11.82 | 16.77 | 10.76 | 16.81 | 8.47 |
| Dethylbenzene | 4.58 | 0.52 | 3.46 | 0.22 | 2.81 | 0.02 | 2.83 | 0.04 |
| Butylbenzene | 0.00 | 0.00 | 0.00 | 0.00 | 0.00 | 0.00 | 0.00 | 0.00 |
| Other C₁₀ | 5.22 | 1.90 | 5.10 | 1.97 | 1.48 | 1.48 | 4.03 | 0.94 |
| C₁₁₊ Heavies | 8.58 | 7.58 | 7.28 | 6.08 | 5.89 | 4.74 | 5.93 | 3.92 |
| Total C₇ + C₈ | 12.44 | 44.29 | 10.73 | 42.87 | 8.97 | 36.99 | 8.85 | 43.75 |
| C₇ + C₈ (−20% o-xylene) | 11.13 | 43.35 | 9.61 | 42.05 | 8.04 | 36.34 | 7.93 | 43.03 |
| EB/C₈ (−20% o-xylene) | 4.80 | 22.81 | 5.21 | 28.31 | 5.81 | 31.56 | 5.81 | 29.04 |
| p-Xyl/C₈ (−20% o-xyl) | 13.29 | 18.81 | 13.19 | 17.37 | 13.18 | 16.61 | 13.16 | 17.32 |

$$Y_a = \frac{A_p - A_f}{F} \quad (2)$$

In Equations (1) and (2), $A_f$ and $A_p$ stand for the weight percent of a Component A in the feed and product, respectively. F stands for the total weight of the feed. $C_a$ and $Y_a$ represent, respectively, the conversion of the Component A and the yield of the Component A. In order to simplify analysis of the experimental work, the cumulative amount of isomers of a compound can be treated as a single component. For example, in this work the three ethyltoluene isomers are added together to provide a single total composite amount which is treated as a single Component A in analysis to arrive at the ethyltoluene conversion or ethyltoluene yield.

The conversion of individual components depends on the feed composition due to equilibrium. As noted previously, constant reaction severity can be maintained by adjusting temperature so that conversion of each individual component remains constant upon change in feed composition. This protocol was followed in the experimental work. The reaction severity was checked intermittently using a pure toluene feed with the temperature adjusted to provide a conversion of 47% when the feed is switched to pure toluene. While it will usually be preferred in practicing the present invention to provide a constant reaction severity by adjustment of the reaction temperature, it will be recognized that other reaction conditions of pressure and space velocity can be adjusted in lieu of temperature adjustment or in combination with adjustment of temperature or another reaction parameter. For example, rather than increasing the temperature in the reaction zone with time to provide a constant reaction severity and to maintain the desired ETCF within the desired equivalence range, the reaction pressure can be increased in conjunction with a more moderate increase in temperature or while maintaining the temperature constant. Similarly, rather than increasing temperature as the process progresses with time, the space velocity can be decreased as necessary to maintain the desired ETCF within the appropriate tolerance range. In summary, one, two, or all three of the reaction conditions of temperature, pressure, and space velocity can be varied in order to arrive at the condition of constant reaction severity. However, it usually will be preferred to progressively increase the temperature while maintaining the other reaction conditions, particularly pressure, constant or relatively constant over the life of the catalyst run.

As noted previously, in considering the progress of the reaction conversions involved in the present invention with time, a somewhat sharper increase in temperature will be involved during the earlier stages of the process with a more moderate increase during the later stages in order to maintain the desired condition of constant reaction severity. As a general rule, in maintaining a constant reaction severity at the desired ETCF value within the range of 40–50%, the temperature will be increased during an early stage of the process at an incremental rate within the range of 1.0–2.0° C. per day. During the latter stages of the process during the life of the catalyst where the plateau condition is reached, the incremental increase in temperature normally will be substantially less than 1° C. per day and typically within the range of about 0.05–0.25° C. per day.

Referring further to Table III, the last four rows of the table present data for the total $C_7+C_8$ yields as well as the ratios of ethylbenzene and para xylene in the $C_8$ fraction. Due to the relatively high boiling point of ortho xylene (144° C.), ortho xylene may not fully recoverable in order to meet the xylene specifications of a refining operation. In a xylene fractionation column, about 20% of ortho xylene may be recovered in the $C_9+$ stream from the bottom of the xylene column. As indicated in Table III, the recoverable $C_7+C_8$ yields, the ethylbenzene/$C_8$ value, and the para xylene/$C_8$ values were calculated by the total $C_7+C_8$ with 20% ortho xylene subtracted.

Turning now to the drawings, FIG. 1 is a graph of certain effluent parameters based upon the data presented in Table III. In FIG. 1 the ethylbenzene and toluene contents C in weight percent are plotted on the ordinate versus the amount of benzene B in weight percent in the heavy aromatic feed. In FIG. 1 curve 2 is a plot of ethylbenzene content over total $C_8$ plotted on the right ordinate. Curves 4, 5, and 6 are graphs of meta xylene, ethylbenzene, ortho xylene and para xylene in weight percent plotted on the left ordinate. In Curve 6 the ortho xylene and meta xylene contents are superimposed upon one another, and only a single curve is shown the illustrate each of the ortho xylene and para xylene contents. As can be seen from an examination of the data plotted in FIG. 1, the yields of ethylbenzene and the xylene isomers varied linearly with the amount of benzene in the feedstock. The xylene content decreased and the ethylbenzene content increased as the percent of benzene in the feed was increased while maintaining a 47% ethyltoluene conversion factor.

Table 4 presents data respecting conversions as defined in Equation (1) above of benzene, ethyltoluene, and trimethylbenzene as a function of the feed ratio of benzene in a benzene/$C_9$+Ar feed over the toluene disproportionation catalyst for operations at a ETCF of 47% for 30%, 40%, and 50% benzene streams and an ETCF in the last column of 53% for a 50% benzene stream. In addition, non-aromatics in the effluent are presented for each of the benzene contents.

TABLE IV

| | $C_6/C_9$ Conversion and $C_6/C_7$ Nonaromatics | | | |
|---|---|---|---|---|
| BZ% in $C_9$Ar Feed | 30 | 40 | 50 | 50* |
| Conversion, wt % | | | | |
| Benzene | 24.42 | 24.69 | 18.62 | 22.24 |
| ET | 57.99 | 55.05 | 59.58 | 71.38 |
| TMB | 33.31 | 41.53 | 36.64 | 50.65 |
| (BZ + TMBs + Ets) | 34.57 | 34.35 | 27.67 | 35.42 |
| Nonaromatics in Effluent | | | | |
| Total, % | 1.40 | 1.17 | 0.99 | 1.19 |
| MCP, ppm | 100 | 94 | 87 | 80 |
| CH, ppm | 43 | 67 | 43 | 23 |
| MCH, ppm | 30 | 37 | 30 | 27 |
| $C_{6-7}$/BZ, wt % | 0.079 | 0.066 | 0.039 | 0.034 |
| $C_{6-7}$/Tol, wt % | 0.090 | 0.102 | 0.091 | 0.057 |

*Reaction severity equivalent to 53%, instead of 47% TDP conversion.

The reaction involved is an equilibrium-driven reaction in which the existence of product molecules will drive the equilibrium back to the reactant. The feed mixture (Table III) had a xylene content within the range of 8.4 to 11.9%, which lowered the overall conversion of benzene and $C_9$ aromatics, mostly compromising ethyltoluene and trimethylbenzene. As shown by the data in Table IV, the conversions of benzene, ethyltoluene, and trimethylbenzene were in the neighborhood of 20%, 60%, and 35%, respectively. The higher activity of the reaction for ethyltoluene relative to trimethylbenzene is due to the ethyl side chains of the aromatic nuclei. As a general rule, the reactivity of the side change exhibited the order of propyl>ethyl>methyl. The conversion of propyl benzene and cumene were over 90%.

Figure 2:
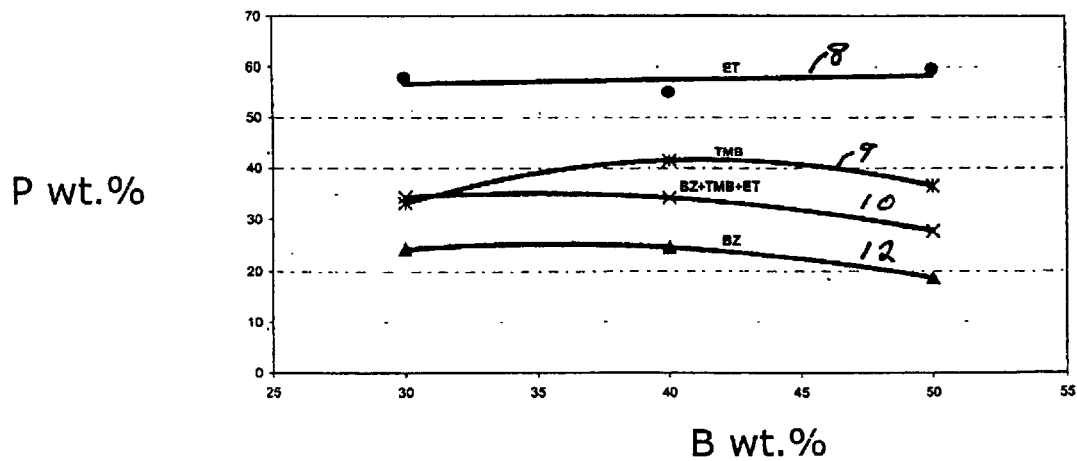
FIG. 2 is a graphical presentation showing the conversion of $C_6$–$C_9$ hydrocarbons as a function of a benzene content of the feedstock.

The conversion of ethyltoluene, toluene, and trimethylbenzene as a function of the benzene/$C_9$+Ar feed ratio is illustrated in FIG. 2 in which weight percent of product components P is plotted on the ordinate versus the weight percent of benzene B in the feed in the abscissa. In FIG. 2, curve 8 illustrates the weight percent of ethyltoluene in the effluent, and curve 9 is a graph of the weight percent of trimethylbenzene in the product. Curves 10 and 12 illustrate the conversions of benzene plus trimethylbenzene plus ethyltoluene and the conversion of benzene, respectively.

Figure 3:
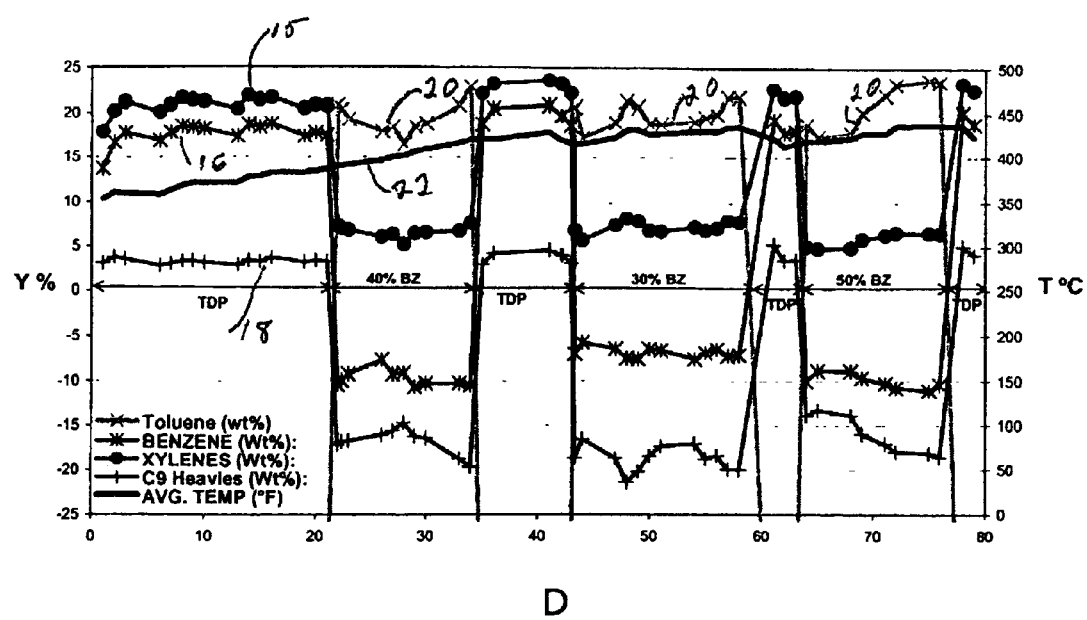
FIG. 3 is a graphical presentation indicating yields and temperature conditions during transalkylation with intervening toluene disproportionation as a function of time during the conversion process.

Turning now to FIG. 3, there is illustrated graphs of benzene, toluene, xylenes, and $C_9$ yield Y from the benzene $C_9$+Ar transalkylation procedure over the 79-day interval described above and summarized in Table II. In addition, the reaction temperature is plotted on the right hand ordinate versus the days on stream D on the abscissa. More specifically, in FIG. 3 curves 15, 16, and 18 are plots of the yields Y in wt. % on the ordinate of xylenes, benzene, and $C_9$ heavies, respectively, as a function of the days on stream D. Results are reported for the intervals designated as step 2, step 4, and step 6 in Table II, with the toluene disproportionation intervals, steps 1, 3, 5, and 7 preceding, intervening, and following the transalkylation intervals. Toluene yield is indicated by curve 20.

The reaction temperature is indicated by curve 22, which is plotted on the right-hand ordinate in ° C. against the days on stream. As noted previously, space velocity is maintained at 3 hrs.$^{-1}$ LHSV, and the reactor pressure is maintained at 40 atmospheres. The relative rapid increase of the reaction temperature to maintain the constant reaction severity at an ETCF value of about 47% increased somewhat sharply to a value of about 420° C., after which it increased at a lower rate to a plateau of about 420–440° C. The deactivation rates before the plateau region and during the plateau region is estimated to be about 1.59 and 0.07° C./day, respectively.

Having described specific embodiments of the present invention, it will be understood that modifications thereof may be suggested to those skilled in the art, and it is intended to cover all such modifications as fall within the scope of the appended claims.

What is claimed:

1. A process for the operation of an aromatic conversion unit comprising:
   (a) providing a catalytic reaction zone containing a metal modified zeolite transalkylation catalyst;
   (b) supplying a toluene-containing feedstock to said reaction zone while operating said reaction zone under conditions effective for the disproportionation of toluene;
   (c) recovering a disproportionation product containing benzene and xylene from said reaction zone;
   (d) terminating the supply of said toluene-containing feedstock to said reaction zone;
   (e) thereafter supplying to said reaction zone containing said metal-modified zeolite catalyst a transalkylation feedstock containing a benzene component and a polyalkylated aromatic component comprising at least one polyalkyl aromatic compound having at least nine carbon atoms;
   (f) operating said reaction zone under conditions effective for the transalkylation of said feedstock to produce a transalkylated product having a reduced polyalkyl benzene content and an enhanced monoalkyl benzene content relative to said transalkylation feedstock; and
   (g) recovering said transalkylated product from said reaction zone.

2. The method of claim 1 wherein said catalyst comprises mordenite.

3. The method of claim 2 wherein said catalyst comprises nickel-modified mordenite.

4. The method of claim 3 wherein said catalyst contains nickel in an amount within the range of 0.1–2.0 wt. %.

5. The method of claim 1 wherein said transalkylation feedstock of paragraph (e) of claim 1 has a weight ratio of said benzene component to said polyalkylated benzene component within the range of 1:9 to 2:1.

6. The method of claim 5 wherein said transalkylation product recovered in paragraph (g) of claim 1 comprises toluene, ethylbenzene, and xylene with a content of $C_7$ and $C_8$ alkyl aromatic compounds within the range of 35–45 wt. %.

7. The method of claim 6 wherein the ethylbenzene content of said transalkylation product is less than one-half of the toluene content.

8. The method of claim 6 wherein the ethylbenzene content of said transalkylation product is less than one-half of said xylene content.

9. The method of claim 6 wherein the ethylbenzene content of said transalkylation product is less than one-half of each of the toluene content and the xylene content.

10. A process for the transalkylation of an aromatic feedstock comprising:
    (a) providing a catalytic reaction zone containing a metal modified zeolite transalkylation catalyst;
    (b) supplying to said reaction zone a transalkylation feedstock containing a benzene component and a polyalkylated aromatic component comprising at least one polyalkyl aromatic compound having at least 9 carbon atoms;
    (c) operating said reaction zone under temperature and pressure conditions providing an equivalent conversion of pure toluene in the presence of said catalyst within the range of 40–55% and effective for the transalkylation of said feedstock to provide a transalkylated product having a reduced polyalkylbenzene content and an enhanced monoalkylbenzene content relative to said transalkylation feedstock; and
    (d) recovering said transalkylated product from said reaction zone.

11. The process of claim 10 wherein said reaction zone is operated under pressure and temperature conditions providing for an equivalent conversion of toluene in the presence of catalyst within the range of 42–48%.

12. The process of claim 10 wherein said reaction zone is operated under pressure and temperature conditions providing for an equivalent conversion of toluene in the presence of catalyst within the range of 45–47%.

13. The method of claim 10 wherein said transalkylation feedstock has a weight ratio of said benzene component to said polyalkylated benzene component within the range of 1:9 to 2:1.

14. The method of claim 13 wherein said transalkylation product comprises toluene, ethylbenzene, and xylene with a content of $C_7$ and $C_8$ alkyl aromatic compounds within the range of 35–45 wt. %.

15. The method of claim 14 wherein the ethylbenzene content of said transalkylation product is less than one-half of the toluene content.

16. The method of claim 14 wherein the ethylbenzene content of said transalkylation product is less than one-half of said xylene content.

17. The method of claim 14 wherein the ethylbenzene content of said transalkylation product is less than one-half of each of the toluene content and the xylene content.

18. The process of claim 10 further comprising:
(a) terminating the supply of said transalkylation feedstock to said reaction zone;
(b) thereafter supplying a toluene rich feedstock to said reaction zone;
(c) operating said reaction zone under temperature and pressure conditions effective for the disproportionation of toluene; and
(e) recovering a disproportionation product containing benzene and xylene from said reaction zone.

19. A process for the transalkylation of an aromatic feedstock comprising:
(a) supplying a transalkylation feedstock containing benzene and a polyalkylated component comprising at least one polyalkyl benzene compound having at least nine carbon atoms to a reaction zone containing a molecular sieve transalkylation catalyst;
(b) operating said reaction zone under conditions of temperature, pressure, and space velocity effective to transalkylate said feedstock to produce a transalkylation product having a reduced polyalkyl benzene content and an enhanced monoalkyl benzene content relative to said transalkylation feedstock while maintaining an equivalent toluene conversion factor within said reaction zone within the range of 40–55%;
(c) recovering said transalkylated product from said reaction zone; and
(d) continuing the operating of said transalkylation reaction zone in accordance with subparagraph (a), (b), and (c) while adjusting at least one of the reaction conditions of temperature, pressure, and space velocity in order to maintain a constant reaction severity to provide a desired equivalent toluene conversion factor within a tolerance range of ±2% while continuing to recover transalkylated product in accordance with subparagraph (c).

20. The process of claim 19 wherein the temperature of said reaction zone is progressively increased to maintain a condition of constant reaction severity.

21. The method of claim 19 wherein said equivalent toluene conversion factor is maintained within the range of 42–48%.

22. The process of claim 19 wherein said equivalent toluene conversion factor is maintained within the range of 45–47%.

23. The process of claim 18 wherein said reaction zone is operated under gas phase conditions.

* * * * *